(12) United States Patent
Yamagata

(10) Patent No.: US 8,340,374 B2
(45) Date of Patent: Dec. 25, 2012

(54) 3-DIMENSIONAL DIAGNOSTIC IMAGING SYSTEM

(75) Inventor: Hitoshi Yamagata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1230 days.

(21) Appl. No.: 11/969,387

(22) Filed: Jan. 4, 2008

(65) Prior Publication Data

US 2008/0298660 A1 Dec. 4, 2008

(30) Foreign Application Priority Data

Jan. 11, 2007 (JP) .................................. 2007-003742

(51) Int. Cl.
*G06K 9/00* (2006.01)
(52) U.S. Cl. ........................................ 382/128; 382/100
(58) Field of Classification Search .................... None
See application file for complete search history.

(56) References Cited

U.S. PATENT DOCUMENTS

| | | | | |
|---|---|---|---|---|
| 5,432,704 A * | 7/1995 | Vouzelaud et al. | ........... | 700/182 |
| 6,019,724 A * | 2/2000 | Gronningsaeter et al. | .... | 600/439 |
| 6,480,732 B1 * | 11/2002 | Tanaka et al. | ................ | 600/425 |
| 2005/0033160 A1 * | 2/2005 | Yamagata et al. | ........... | 600/425 |
| 2005/0085717 A1 * | 4/2005 | Shahidi | ......................... | 600/424 |
| 2005/0085718 A1 * | 4/2005 | Shahidi | ......................... | 600/424 |
| 2005/0251029 A1 * | 11/2005 | Khamene et al. | ............. | 600/427 |
| 2007/0225553 A1 * | 9/2007 | Shahidi | ......................... | 600/103 |
| 2007/0276234 A1 * | 11/2007 | Shahidi | ......................... | 600/437 |
| 2008/0107312 A1 * | 5/2008 | Von Berg | ...................... | 382/128 |

FOREIGN PATENT DOCUMENTS

| | | |
|---|---|---|
| JP | 2002-112998 | 4/2002 |
| JP | 2005-169070 | 6/2005 |
| WO | WO 9625881 A1 * | 8/1996 |

* cited by examiner

*Primary Examiner* — David A Vanore
*Assistant Examiner* — Andrew Smyth
(74) *Attorney, Agent, or Firm* — Oblon, Spivak, McClelland, Maier & Neustadt, L.L.P.

(57) ABSTRACT

A 3-dimensional diagnostic imaging system for acquiring and displaying 3-dimensional images includes an ultrasound diagnostic imaging apparatus configured to display any cross section of a 3-dimensional image extracted from volume data including an affected part of a subject; a 3-dimensional medical diagnostic imaging apparatus configured to display a cross section of a 3-dimensional image extracted from volume data obtained by medical diagnostic imaging modalities other than the ultrasound diagnostic imaging apparatus, the cross section being substantially identical to the cross section displayed by the ultrasound diagnostic imaging apparatus; and an image processing/display unit configured to synchronously display substantially identical cross sections of a plurality of 3-dimensional images from both the ultrasound diagnostic imaging apparatus and the 3-dimensional medical diagnostic imaging apparatus, or to synchronously display substantially identical cross sections of a plurality of 3-dimensional images extracted from volume data obtained by the same medical diagnostic imaging modality at different times.

6 Claims, 11 Drawing Sheets

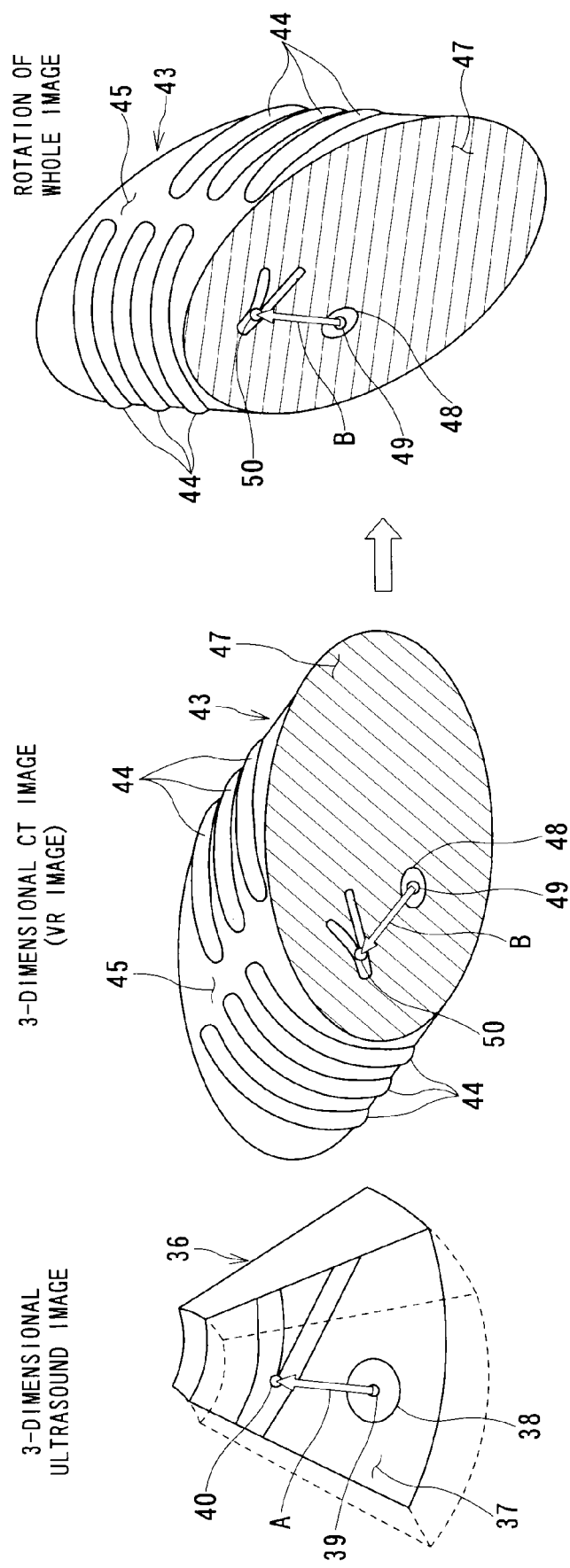

3-DIMENSIONAL DIAGNOSTIC IMAGING SYSTEM

BACKGROUND OF THE INVENTION

1. Field of the Invention

The present invention relates to imaging technology for diagnosis based on 3-dimensional (3D) medical images, and particularly relates to a 3-dimensional diagnostic imaging system for use in locating an affected part and making a differential diagnosis using a 3-dimensional ultrasound image and another type of 3-dimensional diagnostic modality image in a complementary manner.

2. Description of the Related Art

Cancer is one of three major diseases in Japan today. Of the three major diseases, cancer is the only disease with an increasing mortality. Accordingly, there are strong social demands for improved treatment as well as diagnosis of cancer. In particular, liver cancer represents about 10% of all cancer diseases and unfortunately, the mortality from liver cancer is increasing.

As for diagnosis of liver cancer, early detection has been made possible by recent technological advances in medical diagnostic imaging modalities, such as an ultrasound diagnostic imaging apparatus, an MRI scanner, and an X-ray CT scanner.

An X-ray CT scanner realizes a 3-dimensional imaging technique by combining a multiraw (8-raw, 16-raw, 64-raw, or the like) detector with a high-speed helical scanner. With an MRI scanner, 3-dimensional imaging can be performed in a short time with one breath-holding. This is made possible by advances in high-speed imaging techniques associated with improved performance of a gradient magnetic field system, a high-frequency magnetic field system, an RF coil system, and the like. Thus, with advances in 3-dimensional imaging techniques, very high diagnostic ability compared to that achieved by conventional 2-dimensional imaging techniques has been achieved. Particularly significant advances in 3-dimensional diagnostic imaging have been made in 3-dimensional dynamic CT (hereinafter referred to as 3-dimensional CT) with a contrast agent.

As for treatment for liver cancer, the following four types are known: (a) transcatheter arterial embolization, (b) transcatheter arterial chemo-embolization, (c) minimally invasive treatment, and (d) abdominal surgery. Of the four types, minimally invasive treatment is most widely used, as it is less invasive to the patient.

Examples of this minimally invasive treatment include a percutaneous ethanol injection technique (PEIT) and microwave ablation. A minimally invasive treatment is performed with a puncture needle, which is monitored through its real-time image acquired by an ultrasound diagnostic imaging apparatus.

Of various ablation treatments, radio-frequency ablation (RFA) is in the limelight and its clinical application is in progress. Examples of RFA include cool-tip RFA performed with a single needle and RITA performed with a plurality of needles. These ablation treatments are currently under clinical evaluation. In many cases, puncture is performed percutaneously. In some cases, treatment is laparoscopically performed using the same puncture device as described above while observing the surface of the liver or while observing the inside of the liver through its surface using an ultrasound transducer.

However, despite the recent technological advances in 3-dimensional diagnostic imaging and therapeutic/diagnostic puncture, 3-dimensional medical diagnostic images are not effectively used in planning or treatment of puncture or in aftercare. Ultrasound images used in clinical practice are local diagnostic images which do not allow simultaneous observation of the entire liver and adjacent parts, such as a diaphragm and the like. Thus, there is a need for techniques that make it possible to easily find a proper needle insertion point on a 3-dimensional CT image.

Moreover, since therapeutic puncture is performed by means of ultrasound imaging, there is a need to display, on a 3-dimensional image, an easy-to-understand 3-dimensional CT cross-sectional image (virtual ultrasound image) representing a possible image of an ultrasound cross section including a puncture needle to be observed during puncture treatment. There is also a need to display a determined needle insertion point relative to a body surface and bones.

In recent years, there have been proposed various techniques for displaying a virtual ultrasound cross-sectional image superimposed on a 3-dimensional CT image, for example, in JP-A 2002-112998, JP-A 2005-169070, or US 2005/0033160 A1. Thus, real-time virtual ultrasound imaging systems have been commercially available.

JP-A 2002-112998 proposes a puncture assisting apparatus for displaying, on the basis of 3-dimensional volume data, a cross section image according to the position and angle of an ultrasound transducer used in puncture. However, with this assisting apparatus, it is difficult to determine whether there is an obstacle on or near the path along which to insert a puncture needle.

In a technique for displaying a virtual ultrasound cross-sectional image superimposed on a 3-dimensional CT image, there is a problem in that a part to be treated can be seen only on an X-ray CT image and cannot be seen or cannot be easily seen on an ultrasound diagnostic image. Another problem is that if there are two or more parts to be treated, it is difficult to perform effective treatment on the basis only of images obtained in planning of treatment.

Also, in a technique for displaying a virtual ultrasound cross-sectional image superimposed on a 3-dimensional CT image, due to characteristics of ultrasound puncture treatment, an ultrasound image displayed on an ultrasound diagnostic imaging apparatus is a 2-dimensional cross-sectional image. Such a 2-dimensional cross-sectional image is limited to a CT cross-sectional image or the like that is substantially identical to a cross-sectional image acquired at a position which allows acquisition of an image with an ultrasound transducer. Therefore, it is difficult to make comparison, after treatment, among images acquired by different modalities.

SUMMARY OF THE INVENTION

The present invention has been made in view of the circumstances described above. An object of the present invention is to provide a 3-dimensional diagnostic imaging system which allows comparison of any cross sections between a 3-dimensional ultrasound image and a 3-dimensional diagnostic modality image for complementary purposes, and thus makes it possible to perform effective and efficient detection and differential diagnosis of a disease, such as cancer.

Another object of the present invention is to provide a 3-dimensional diagnostic imaging system which allows easy and simple comparison of cross sections between a local ultrasound image and an overall 3-dimensional diagnostic modality image for complementary purposes, by using a 3-dimensional ultrasound image and without using a cross-sectional image that can be acquired only at a position which allows acquisition of an image with an ultrasound transducer.

To solve the problems described above, according to an aspect of the present invention, a 3-dimensional diagnostic imaging system for acquiring and displaying 3-dimensional images includes an ultrasound diagnostic imaging apparatus configured to display any cross section of a 3-dimensional image extracted from volume data including an affected part of a subject; a 3-dimensional medical diagnostic imaging apparatus configured to display a cross section of a 3-dimensional image extracted from volume data obtained by medical diagnostic imaging modalities other than the ultrasound diagnostic imaging apparatus, the cross section being substantially identical to the cross section displayed by the ultrasound diagnostic imaging apparatus; and an image processing/display unit configured to synchronously display substantially identical cross sections of a plurality of 3-dimensional images from both the ultrasound diagnostic imaging apparatus and the 3-dimensional medical diagnostic imaging apparatus, or to synchronously display substantially identical cross sections of a plurality of 3-dimensional images extracted from volume data obtained by the same medical diagnostic imaging modality at different time points.

In diagnosis and evaluation of therapeutic effects using a 3-dimensional ultrasound image acquired by an ultrasound diagnostic imaging apparatus, the 3-dimensional diagnostic imaging system of the present invention allows the user to refer to a 3-dimensional diagnostic modality image (3-dimensional reference image) acquired by a medical diagnostic imaging modality other than the ultrasound diagnostic imaging apparatus, and make a simple comparison of common cross sections between the 3-dimensional ultrasound image and the 3-dimensional reference image, which are complementary to each other. The 3-dimensional diagnostic imaging system of the present invention also allows a simple comparison of common cross sections between 3-dimensional diagnostic modality images of different time phases. Thus, the user can reliably, efficiently, and effectively identify the presence, size, and content of a part affected with cancer or the like and make an accurate differential diagnosis.

BRIEF DESCRIPTION OF THE DRAWINGS

FIG. 6A, FIG. 6B, and FIG. 6C illustrate a 3-dimensional ultrasound image and a 3-dimensional CT image displayed on the left and right sides of a monitor of an ultrasound diagnostic imaging apparatus (or a 3-dimensional image display unit of the standalone image processing/display apparatus).

DESCRIPTION OF THE PREFERRED EMBODIMENTS

Embodiments of a 3-dimensional diagnostic imaging system according to the present invention will now be described with reference to the attached drawings.

First Embodiment

Figure 1:
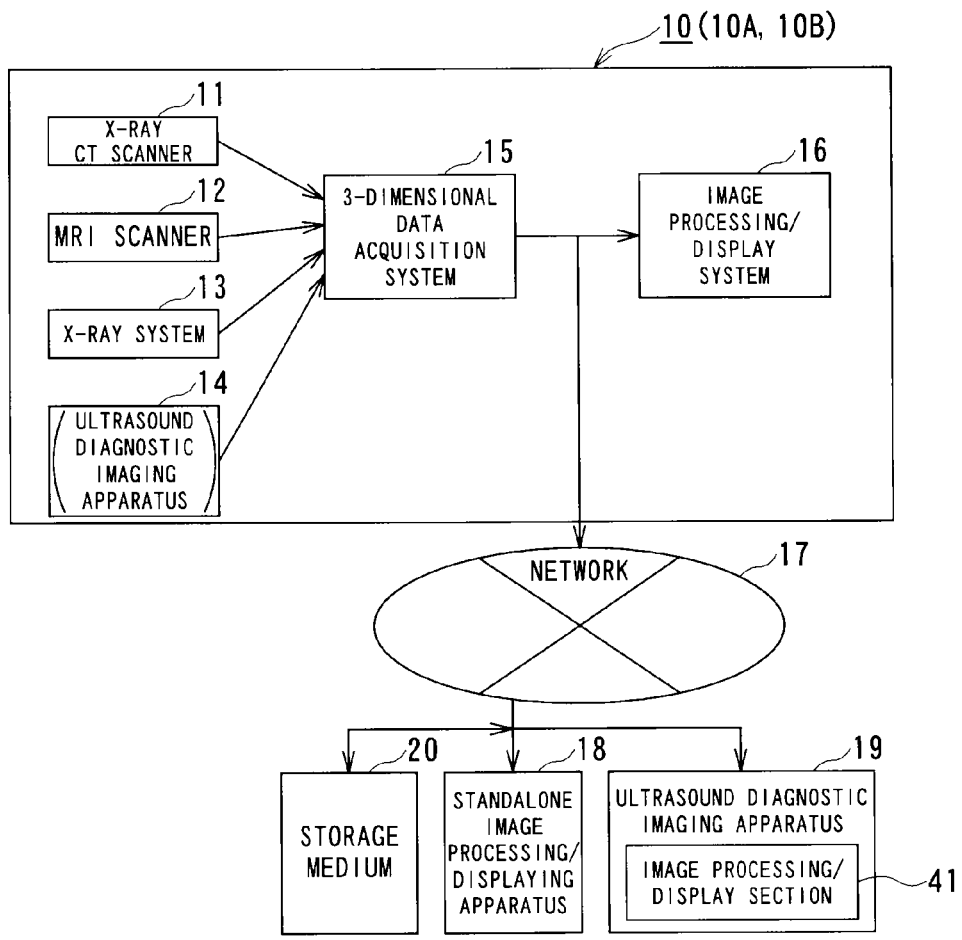
FIG. 1 illustrates an overall structure of a 3-dimensional diagnostic imaging system according to a first embodiment of the present invention.

FIG. 1 is a schematic diagram illustrating an overall structure of a 3-dimensional diagnostic imaging system according to a first embodiment of the present invention.

A 3-dimensional diagnostic imaging system 10 includes a 3-dimensional data acquisition system 15 for acquiring 3-dimensional volume data of a part to be diagnosed and an image processing/display system 16 for processing and displaying the 3-dimensional volume data acquired by the 3-dimensional data acquisition system 15. The 3-dimensional volume data acquired by the 3-dimensional data acquisition system 15 is obtained by an X-ray CT scanner 11, a magnetic resonance imaging (MRI) scanner 12, an X-ray system 13, or an ultrasound diagnostic imaging apparatus 14 (hereinafter, these are collectively referred to as medical diagnostic imaging modalities). Here, the 3-dimensional volume data is an image data acquired by a 3-dimensional imaging method or a multi-slicing imaging method. The 3-dimensional data acquisition system 15 may be included in each medical diagnostic imaging modality.

The 3-dimensional volume data obtained by each medical diagnostic imaging modality may be displayed on a console monitor (not shown) using a image processing/display function of each diagnostic modality, on a display unit of the image processing/display system 16, on a display unit of an standalone image processing/display apparatus 18, or on a display unit of an ultrasound diagnostic imaging apparatus 19.

The following description refers to the case in which, of 3-dimensional diagnostic modality images that can be obtained by the X-ray CT scanner 11, MRI scanner 12, X-ray system 13, and ultrasound diagnostic imaging apparatus 14, the 3-dimensional diagnostic imaging system 10 of the first embodiment uses a 3-dimensional CT image.

A 3-dimensional CT image acquired by the 3-dimensional data acquisition system 15 may be directly displayed on the image processing/display system 16, or the resulting image may be displayed via a network 17 (e.g., LAN) on the display unit of the standalone image processing/display apparatus 18 or on the display unit of the ultrasound diagnostic imaging apparatus 19. The display unit of the ultrasound diagnostic imaging apparatus 19 is capable also of displaying a real-time image of a puncture needle inserted into a subject's body.

Although FIG. 1 illustrates the ultrasound diagnostic imaging apparatuses 14 and 19 as being separated from each other, they may be provided as a single unit.

A 3-dimensional image acquired by a medical diagnostic imaging modality is displayed on a monitor 32 (see FIG. 3) serving as a display unit of the ultrasound diagnostic imaging apparatus 19. The 3-dimensional volume data described above is transferred, in DICOM format or the like, directly or indirectly from each medical diagnostic imaging modality to the ultrasound diagnostic imaging apparatus 19 and stored in a storage medium, such as a CD-R or a DVD-R, in the ultrasound diagnostic imaging apparatus 19.

Figure 2:
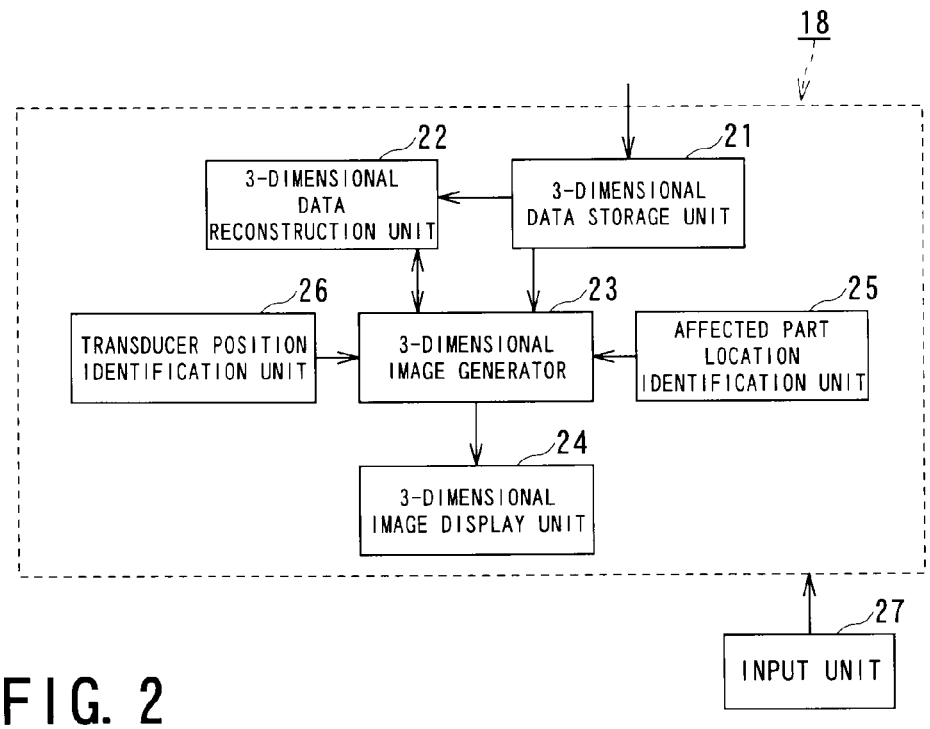
FIG. 2 is a block diagram of a standalone image processing/display apparatus included in the 3-dimensional diagnostic imaging system of FIG. 1.

As illustrated in FIG. 2, the standalone image processing/display apparatus 18 includes a 3-dimensional data storage unit 21 for storing 3-dimensional volume data acquired via the network 17; a 3-dimensional data reconstruction unit 22 for reconstructing the 3-dimensional data stored in the 3-dimensional data storage unit 21; a 3-dimensional image generating unit 23 for generating a 3-dimensional image from data reconstructed by the 3-dimensional data reconstruction unit 22; a 3-dimensional image display unit 24 for displaying a 3-dimensional image on the basis of data generated by the 3-dimensional image generating unit 23; an affected part location identification unit 25 for allowing a user, such as a doctor, to identify the location of an affected part by supplying information indicating the location of an affected part to the 3-dimensional image generating unit 23 on the basis of an affected part included in a cross-sectional image displayed on the 3-dimensional image display unit 24; and a transducer position identification unit 26 for identifying the position of a puncture transducer and supplying data indicating the identified position to the 3-dimensional image generating unit 23. The 3-dimensional data storage unit 21 includes a storage medium, such as a semiconductor memory, a hard disk, a CD-ROM, a flexible disk, or a memory card.

The standalone image processing/display apparatus 18 is, for example, a workstation and is controlled by a CPU (not shown). Alternatively, the standalone image processing/display apparatus 18 having the same processing and displaying capability may be included in the ultrasound diagnostic imaging apparatus 19.

An input unit 27 serves as an interface with which the user inputs various instructions to the standalone image processing/display apparatus 18. As will be described below, various instructions for setting a puncture path are input from the input unit 27. If the standalone image processing/display apparatus 18 is a workstation, the input unit 27 includes a keyboard, a mouse, and/or the like. If the standalone image processing/display apparatus 18 is included in the ultrasound diagnostic imaging apparatus 19, the input unit 27 includes an operation panel, a trackball, a touch command screen (TCS), and/or the like.

The ultrasound diagnostic imaging apparatus 19 has a monitor which displays an image of an affected part of a subject's body and a puncture needle, the image being acquired with an ultrasound transducer during puncture. Although, in the present embodiment, the ultrasound diagnostic imaging apparatus 19 is used for puncture, another type of apparatus, such as an X-ray CT scanner or an MRI scanner, may be used instead.

Figure 3:
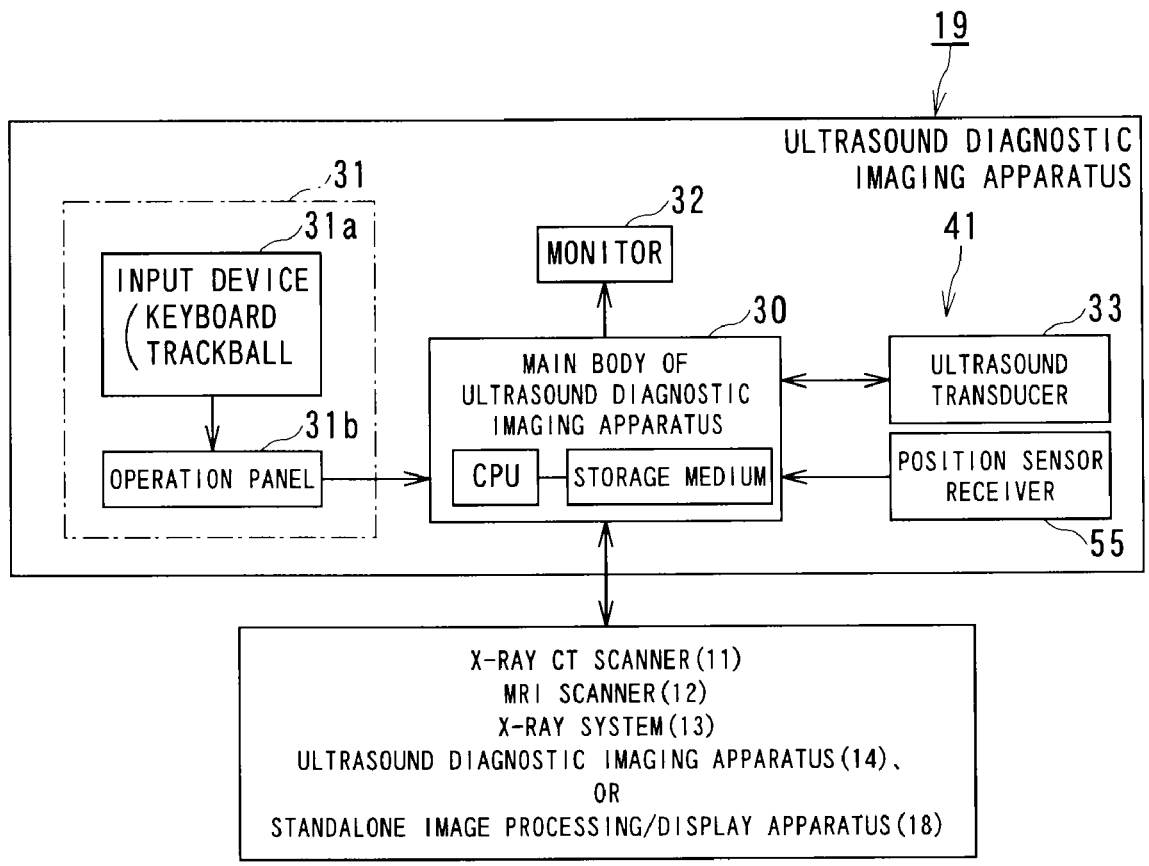
FIG. 3 illustrates a structure of an ultrasound diagnostic imaging apparatus included in the 3-dimensional diagnostic imaging system of FIG. 1.

As roughly illustrated in FIG. 3, the ultrasound diagnostic imaging apparatus 19 includes an main body 30 with a CPU, an input unit 31 attached to the main body 30, the monitor 32 serving as a display unit, an ultrasound transducer 33, and a position sensor receiver 55 for the ultrasound transducer 33. The input unit 31 includes an input device 31a, such as a keyboard and/or a trackball, and an operation panel 31b, such as a touch panel.

The monitor 32 of the ultrasound diagnostic imaging apparatus 19 displays a 3-dimensional image from 3-dimensional volume data. The 3-dimensional volume data is transferred, in DICOM format or the like, from the X-ray CT scanner 11, MRI scanner 12, or X-ray system 13 directly to the main body 30 of the ultrasound diagnostic imaging apparatus 19, or indirectly via a DICOM server or the like to the main body 30. Then, the 3-dimensional volume data is stored in a storage medium, such as a CD-R or a DVD-R, in the main body 30.

The CPU in the main body 30 of the ultrasound diagnostic imaging apparatus 19 performs an image display function, including ultrasound transmission control or 3-dimensional rendering of ultrasound images. The ultrasound transducer 33 and the input unit 31 are connected to the main body 30. An ultrasound image and another type of modality image are displayed on the monitor 32. The main body 30, input unit 31, ultrasound transducer 33, and monitor 32 constitute an image processing/display section (image processing/display unit) 41 in the ultrasound diagnostic imaging apparatus 19. The image processing/display section 41 may also be included in the image processing/display system 16 or standalone image processing/display apparatus 18.

Typically, the ultrasound transducer 33 is a 1-dimensional array transducer, a mechanical 3-dimensional transducer for detecting a plurality of ultrasound cross sections by mechanically vibrating a 1-dimensional array transducer, or a real-time 3-dimensional transducer using a 2-dimensional (matrix) array of a piezoelectric vibrator.

A typical workflow of the 3-dimensional diagnostic imaging system 10 will now be described with reference to FIG. 3.

First, for example, the X-ray CT scanner 11 or a medical diagnostic imaging modality acquires a 3-dimensional CT image (hereinafter may be referred to as 3-dimensional reference image or 3-dimensional diagnostic modality image). Then, 3-dimensional volume data of the acquired 3-dimensional reference image is temporarily placed in the 3-dimensional data acquisition system 15 (step S1).

The volume data of the 3-dimensional reference image is transferred, in DICOM format or the like, from the X-ray CT scanner 11 or 3-dimensional data acquisition system 15 directly to the ultrasound diagnostic imaging apparatus 19, or indirectly via a DICOM server or the like to the ultrasound diagnostic imaging apparatus 19. Alternatively, a 3-dimensional reference image recorded in advance in a storage medium 20, such as an MO, a CD-R, or a DVD-R, is input to the ultrasound diagnostic imaging apparatus 19. The 3-dimensional volume data input to the ultrasound diagnostic imaging apparatus 19 is displayed as a 3-dimensional CT image, for example, on the right side of the monitor 32 by volume rendering (VR) (step S2).

As described above, the ultrasound diagnostic imaging apparatus 19 includes the ultrasound transducer 33, such as a 1-dimensional array ultrasound transducer, a mechanical 3-dimensional transducer, or a real-time 3-dimensional transducer with 2-dimensional array ultrasound transducer. With the ultrasound transducer 33, a 3-dimensional ultrasound image including an affected area is acquired using a B-mode imaging method or a 3-dimensional Doppler imaging method containing a B-mode image. Then, 3-dimensional volume data in the acquired 3-dimensional ultrasound image is input to the main body 30 of the ultrasound diagnostic imaging apparatus 19. The 3-dimensional volume data input to the main body 30 is displayed as a 3-dimensional ultrasound image, for example, on the left side of the monitor 32 by volume rendering (step S3).

In the 3-dimensional diagnostic imaging system 10 of the present embodiment, a 3-dimensional reference image (3-dimensional CT image or 3-dimensional diagnostic modality image) is displayed, for example, on the right side of the monitor 32 of the ultrasound diagnostic imaging apparatus 19, and a 3-dimensional ultrasound image 36 acquired by the ultrasound diagnostic imaging apparatus 19 is displayed, for example, on the left side of the monitor 32. Alternatively, the 3-dimensional diagnostic imaging system 10 may be configured such that the 3-dimensional reference image and 3-dimensional ultrasound image 36 displayed on the monitor 32 of the ultrasound diagnostic imaging apparatus 19 can also be displayed on the 3-dimensional image display unit 24 of the standalone image processing/display apparatus 18.

Figure 4C:
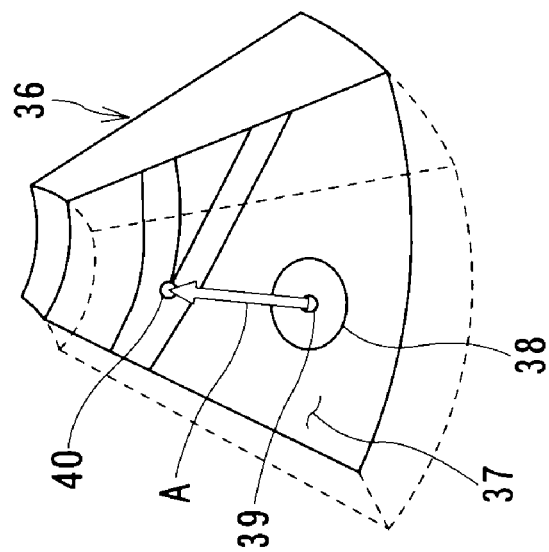
FIG. 4A, FIG. 4B, and FIG. 4C illustrate 3-dimensional ultrasound images acquired by an ultrasound diagnostic imaging apparatus and examples of image processing performed on these images.
Figure 4B:
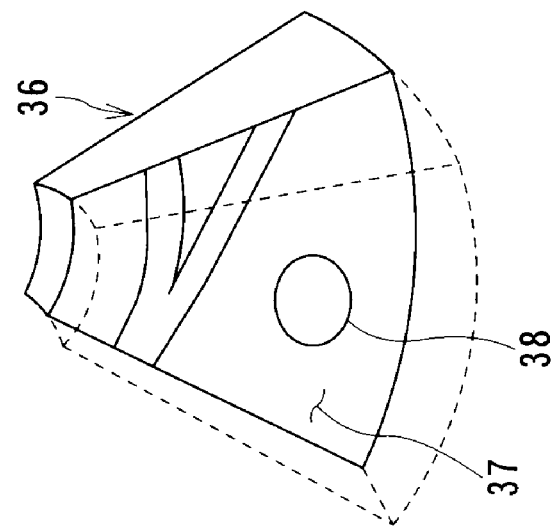
Figure 4A:
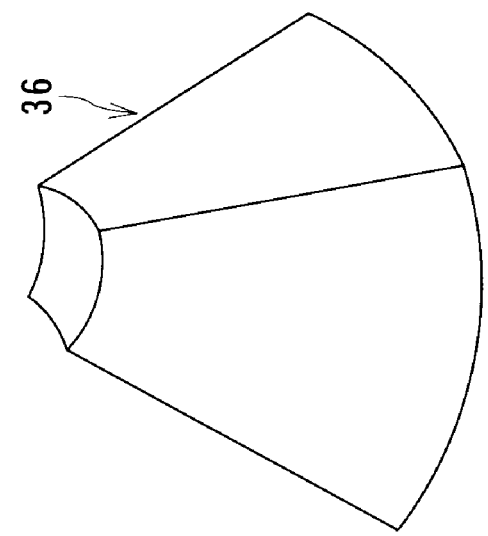

The 3-dimensional ultrasound image 36 acquired by the ultrasound diagnostic imaging apparatus 19 will now be discussed in detail. When the ultrasound transducer 33 is operated, the ultrasound diagnostic imaging apparatus 19 acquires the local 3-dimensional ultrasound image 36 (see FIG. 4A) showing a portion including a possible affected area. The acquired 3-dimensional ultrasound image 36 is displayed, for example, on the left side of the monitor 32. Alternatively, the 3-dimensional ultrasound image 36 may be acquired from the ultrasound diagnostic imaging apparatus 14, which is a medical diagnostic imaging modality. Then, as illustrated in FIG. 4B, a plane cut (PC) 37 is displayed by selecting any cross section on the 3-dimensional ultrasound image 36. That is, in response to rotating and shifting operation using the input unit 31, the CPU in the main body 30 of the ultrasound diagnostic imaging apparatus 19 causes the monitor 32 to display the plane cut 37 as an appropriate positioning cross section, which is a cross section to be subjected to positioning on the 3-dimensional ultrasound image 36. A cross section selected as a positioning cross section and displayed as the plane cut 37 is one that includes an affected part 38. As illustrated in FIG. 4C, for efficient diagnosis, any one point in the affected part 38 is specified as a center locking point 39 (step S4). Typically, a tip point of the puncture needle to be planned is specified as a center locking point 39.

By operating the input unit 31, the plane cut 37 of the 3-dimensional ultrasound image 36 is rotated about a center locking point 39 specified in the affected part 38 as illustrated in FIG. 4C. Thus, the image of a plane cut to be subjected to positioning (i.e., ultrasound diagnostic image) is displayed (step S5).

Then, as illustrated in FIG. 4C, a point representing a structure with a feature different from that represented by the center locking point 39 is selected as a feature point 40. For example, a branching point of a hepatic vein is selected and set as the feature point 40 using the input unit 31. Then, by operating the input unit 31, a line connecting the center locking point 39 and the feature point 40 is graphically displayed as a directional vector line A in a screen coordinate system on the monitor 32 (step S6).

Figure 5A:
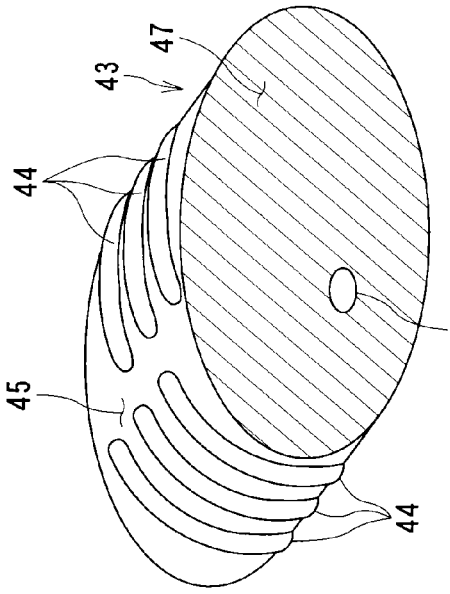
FIG. 5A, FIG. 5B, FIG. 5C, and FIG. 5D illustrate VR images (3-dimensional CT images or 3-dimensional reference images) acquired by a medical diagnostic imaging modality and examples of image processing performed on these images.

At the same time, as illustrated in FIG. 5A, a 3-dimensional CT image 43 acquired by the X-ray CT scanner 11, which is a medical diagnostic imaging modality, is processed by volume rendering and displayed on the monitor 32 of the ultrasound diagnostic imaging apparatus 19. The 3-dimensional CT image 43 allows an observation of a larger area including not only an affected part of the subject's body but also, for example, neighboring parts with distinctive features. The 3-dimensional CT image 43 of the subject's body may be displayed such that a region 44 corresponding to CT values representing bones and the other region 45 are simultaneously displayed by adjusting the transparency in volume rendering, or such that the two regions 44 and 45 are simultaneously displayed as separate volumes (step S7). Reference numeral 47 denotes a plane cut indicating a tentative position of a cross section.

Then, when a user, such as a doctor, specifies the amount and direction of movement or the amount and direction of rotation by moving or rotating a pointing device, such as a mouse or a trackball, in the input unit 31 of FIG. 3, the plane cut 47 of a VR image (3-dimensional reference image or 3-dimensional CT image) of 3-dimensional volume is moved in parallel or rotated by the specified amount in the specified direction and displayed by the CPU of the main body 30.

Figure 5B:
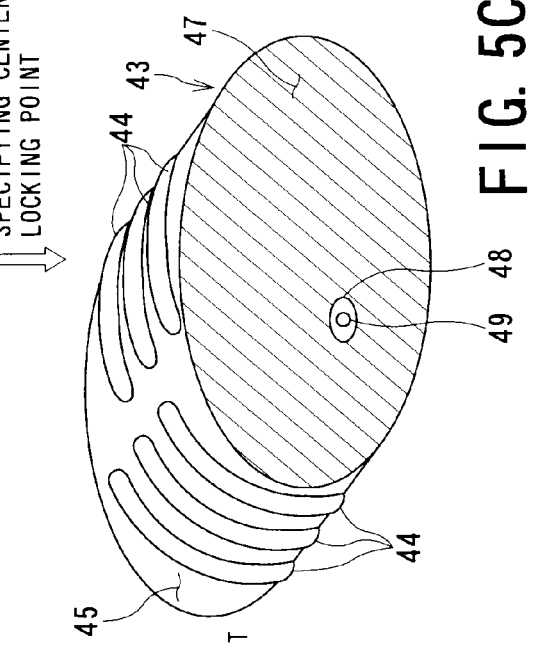

The 3-dimensional reference image (3-dimensional CT image) generated by volume rendering and displayed, for example, on the right side of the monitor 32 of the ultrasound diagnostic imaging apparatus 19 is changed from the state shown in FIG. 5A to that shown in FIG. 5B by shifting and rotating the plane cut 47. Thus, an affected part 48 is located and displayed (step S8).

In the next step, any one point (the point being in the substantially same position as the position of the center locking point 39 specified on the above-mentioned ultrasound image) in the affected part 48 displayed as illustrated in FIG. 5B is specified and set as a center locking point 49. Thus, the plane cut 47 of the 3-dimensional reference image is displayed as illustrated in FIG. 5C (step S9). Next, the plane cut 47 of the VR image (3-dimensional reference image) is rotated about the center locking point 49. Then, as illustrated in FIG. 5D, the plane cut 47 including a feature point 50 and showing the same structure as that shown by the plane cut 37 in the 3-dimensional ultrasound image 36 of FIG. 4C is displayed.

Figure 5D:
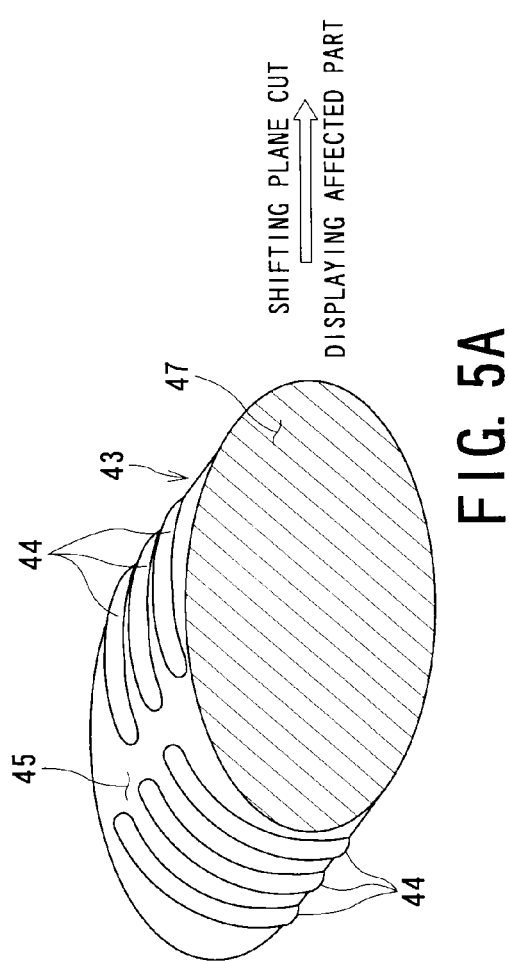
Figure 5C:
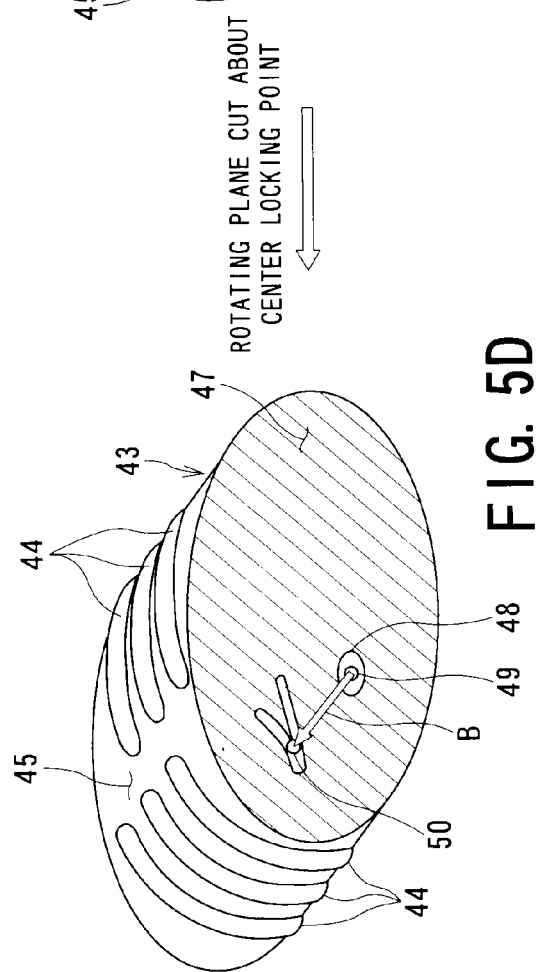

That is, in FIG. 5D, a point representing the same structure as that represented by the feature point 40 of FIG. 4C is set as the feature point 50 of the VR image (3-dimensional reference image or 3-dimensional CT image). Thus, the plane cut 47 including the feature point 50 corresponding to the feature point 40 is displayed. Then, a line connecting the center locking point 49 (rotation center) and the feature point 50 is graphically displayed as a directional vector line B on the VR image (3-dimensional CT image) (step S10).

By shifting and rotating the plane cut 37 of the 3-dimensional ultrasound image 36 (see FIG. 4C) and the plane cut 47 of the 3-dimensional CT image 43 (see FIG. 5D) using the input unit 31 of the ultrasound diagnostic imaging apparatus 19, the plane cuts 37 and 47 and the directional vector lines A and B are displayed on the left and right sides of the monitor 32, respectively. Then, the center locking points 39 and 49 and the directional vector lines A and B are made coincident with each other and thus, cross sections corresponding to each other are displayed (step S11). Then, the center locking points 39 and 49 are fixed by a locking unit (not shown) in the main body 30 of the ultrasound diagnostic imaging apparatus 19. Thus, the 3-dimensional ultrasound image 36 and the 3-dimensional CT image 43 are set such that one of the images automatically follows the movement of the other. With this setting, if one 3-dimensional image is manipulated, the other 3-dimensional image is rotated or moved synchronously therewith in such a manner that it follows the rotation or movement of the manipulated image.

That is, after the corresponding plane cuts 37 and 47 of the 3-dimensional ultrasound image and the 3-dimensional reference image (3-dimensional CT image or VR image) are synchronously displayed on the monitor 32, when a simultaneous display/control function incorporated in the main body 30 of the ultrasound diagnostic imaging apparatus 19 is activated by operating the input unit 31, these 3-dimensional images are rotated and moved substantially synchronously in such a manner that one follows or tracks the other. With this synchronous tracking control, the entire volume of, for example, the 3-dimensional reference image is rotated from the state of FIG. 6B to the state of FIG. 6C and set such that the directional vector lines A and B are oriented in the same direction (see FIG. 6A and FIG. 6C) and that the plane cut 47 of the 3-dimensional CT image (3-dimensional reference image) showing a large area and the plane cut 37 of the 3-dimensional ultrasound image showing a specific local area are oriented in the same direction (see FIG. 6A and FIG. 6C) (step S12).

After this setting is made, the main body 30 of the ultrasound diagnostic imaging apparatus 19 performs control and adjustment such that the manipulation of the 3-dimensional ultrasound image 36 and the 3-dimensional CT image (3-dimensional CT image) 43 is made via the locking unit with the tracking relationship between the two images maintained, and that the 3-dimensional ultrasound image 36 and the 3-dimensional CT image 43 are synchronously moved in response to the operation of the input unit 31 (step S13). Since these two 3-dimensional images are thus moved in synchronization with each other, there is no need to manipulate both images with the input unit 31.

More specifically, rotation and shifting of a plane cut (37 or 47) and various image clipping operations performed on one 3-dimensional image occur synchronously on the other 3-dimensional image, and the resulting 3-dimensional images are displayed synchronously.

When the locking unit is deactivated by unlocking operation performed with the input unit 31, the function of the locking unit is cancelled. Since this terminates the tracking and synchronous operation of the 3-dimensional ultrasound image 36 and 3-dimensional reference image (3-dimensional CT image) 43, shifting and rotating operations on one 3-dimensional image are performed independent of those on the other image. As described above, the input unit 31 serves as an unlocking unit capable of deactivating the locking unit.

The 3-dimensional diagnostic imaging system 10 of the present embodiment makes it possible to simultaneously display the 3-dimensional ultrasound image 36 showing a specific local area including an affected part and the 3-dimensional CT image (3-dimensional diagnostic modality image or 3-dimensional reference image) 43 showing an entire area to be examined, on the left and right sides of the monitor 32 of the ultrasound diagnostic imaging apparatus 19. This allows the user to view a specific local area shown by the 3-dimensional ultrasound image 36 while checking a larger area shown by the 3-dimensional CT image 43, and thus to determine a puncture needle insertion point for observation and diagnosis. For minimally invasive treatment, the 3-dimensional diagnostic imaging system 10 allows the user to simultaneously observe the subject's body surface, bones, whole liver, and neighboring tissues including the diaphragm while monitoring a puncture needle insertion point. Thus, the user can easily find a safe needle insertion point on a 3-dimensional CT image.

The 3-dimensional diagnostic imaging system 10 allows the user to refer to different 3-dimensional diagnostic modality images acquired in advance for the purpose of diagnosis or evaluation of treatment by means of an ultrasound diagnostic imaging apparatus; make an easy comparison of common cross sections between a 3-dimensional ultrasound image and a 3-dimensional reference image (3-dimensional diagnostic modality image) which are complementary to each other; reliably identify the presence, size, location, and content of an affected part; and thus efficiently and effectively perform a differential diagnosis of a disease, such as cancer.

That is, the 3-dimensional diagnostic imaging system of the present invention makes it possible to display in parallel the 3-dimensional ultrasound image 36 serving as a reference 3-dimensional image and showing a specific local area including an affected part and the 3-dimensional CT image (3-dimensional diagnostic modality image) 43 showing tissues in a larger area including the affected part, on the left and right sides (or in the upper and lower parts) of the monitor 32 of the ultrasound diagnostic imaging apparatus 19. Thus, the user can select a 3-dimensional CT image with reference to any cross section of the 3-dimensional ultrasound image 36. That is, with reference to the 3-dimensional ultrasound image 36 (see FIG. 4C) having the plane cut 37 including the affected part 38 and the feature point 40 (e.g., a branching point of hepatic vein or portal vein) representing a distinctive neighboring structure, shifting and rotating operations are performed on the 3-dimensional CT image (3-dimensional reference image, VR image, or 3-dimensional diagnostic modality image) 43, which is then positioned as illustrated in FIG. 5D.

As illustrated in FIG. 6C, by shifting and rotating the 3-dimensional CT image (3-dimensional diagnostic modality image) 43 showing tissues in a larger area including an affected part, the 3-dimensional ultrasound image 36 of FIG. 6A and the 3-dimensional CT image 43 of FIG. 6C are displayed on the monitor 32 of the ultrasound diagnostic imaging apparatus 19 in such a manner that the plane cuts 37 and 47 substantially correspond to each other. The same image display may also be realized on the display unit of the image processing/display system 16 or on the display unit of the standalone image processing/display apparatus 18.

There has been described an example in which the 3-dimensional diagnostic imaging system 10 makes it possible to display the 3-dimensional ultrasound image 36 and the 3-dimensional CT image 43 on the monitor 32. Alternatively, a plurality of 3-dimensional images taken at different time points (i.e., 3-dimensional images of different time phases) may be input to a single medical diagnostic imaging modality and displayed on a display unit. For example, two 3-dimensional ultrasound images (3-dimensional diagnostic modality images) of different time phases may be input to the ultrasound diagnostic imaging apparatus 19 or 14 and displayed on the left and right sides (or in the upper and lower parts) of the monitor 32. This allows a comparison between plane cuts of 3-dimensional ultrasound images of different time phases, such as preoperative and postoperative images.

That is, the 3-dimensional diagnostic imaging system 10 makes it possible to synchronously display on a display unit (e.g., monitor) a plurality of 3-dimensional images acquired by the same medical diagnostic imaging modality at different time points. This allows the user to observe common plane cuts of different 3-dimensional images; accurately and precisely identify the alternation of a part affected by cancer and the vicinity of the part before and after the therapeutics; and determine a therapeutic effect accurately and efficiently.

Figure 7A:
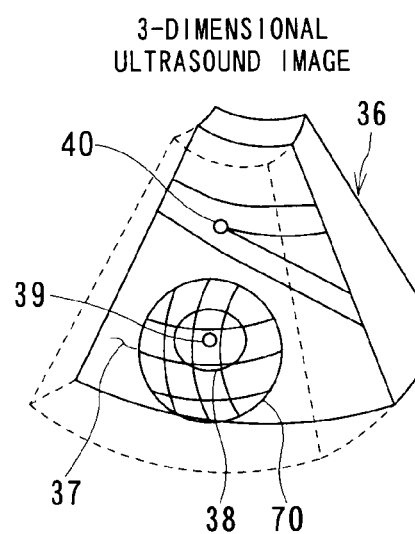
FIG. 7A and FIG. 7B illustrate a 3-dimensional ultrasound image and a 3-dimensional CT image, with spherical regions thereon, which are synchronously displayed on the left and right sides of the monitor of the ultrasound diagnostic imaging apparatus.
Figure 7B:
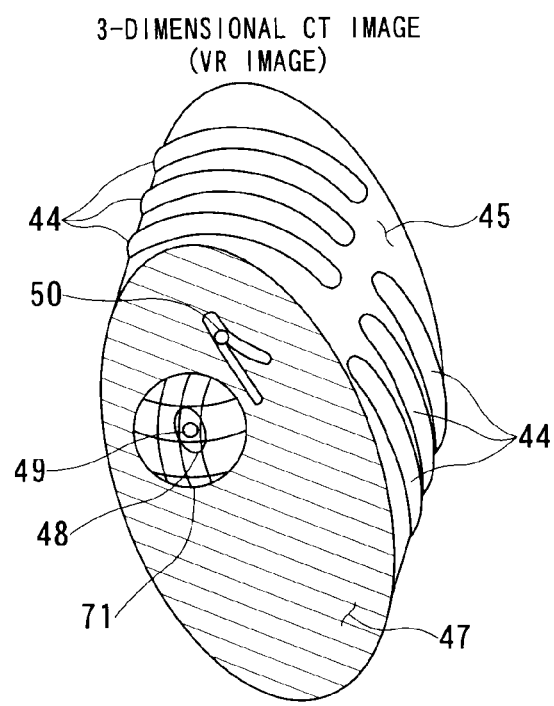

As illustrated in FIG. 7A and FIG. 7B, in the simultaneous display of the 3-dimensional ultrasound image 36 and 3-dimensional CT image 43 with the affected parts 38 and 48, a spherical region 70 and a spherical region 71 may be displayed in the plane cut 37 and the plane cut 47, respectively.

The spherical regions 70 and 71 displayed on a display unit, such as a monitor, as illustrated in FIGS. 7A and 7B indicate planned ablation parts. Displaying a planned ablation part beforehand helps the user determine whether the planned ablation part fully covers the affected part, or precisely evaluate the risk regarding the influence on the organs in the vicinity of the planned ablation part, such as a heart, a lung, and a gall bladder. Since energy typically diffuses in a spherical form, it is reasonable to graphically show the ablation parts as the spherical regions 70 and 71. Thus, on the basis of the 3-dimensional images 36 and 43 showing both overall and specific local areas including the affected part, the user performs an observation so as not to adversely affect neighboring tissues and makes a differential diagnosis.

Figure 8A:
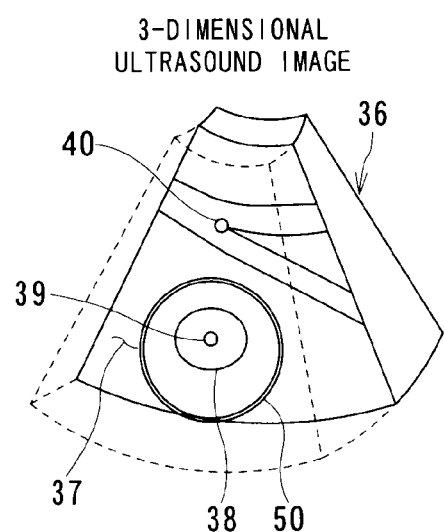
FIG. 8A and FIG. 8B illustrate a 3-dimensional ultrasound image and a 3-dimensional CT image, with circular regions thereon, which are synchronously displayed on the left and right sides of the monitor of the ultrasound diagnostic imaging apparatus.
Figure 8B:
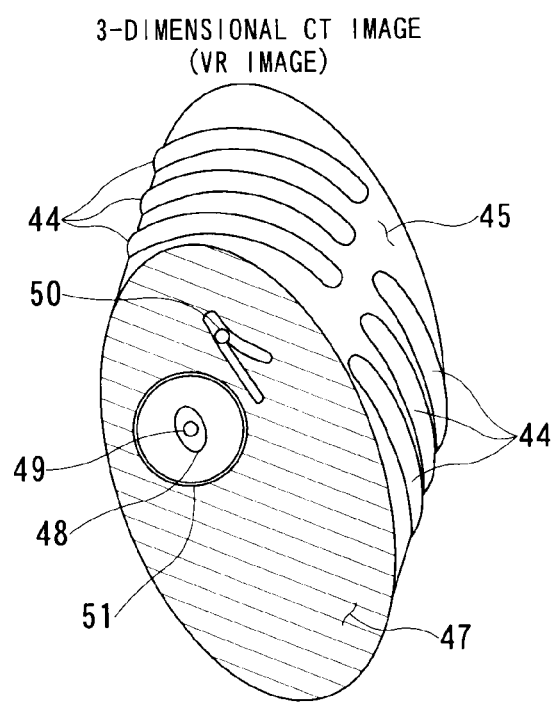

As illustrated in FIG. 8A and FIG. 8B, for purposes similar to those described above, the lines of intersection of the spherical regions 70 and 71 and the plane cuts 37 and 47, respectively, may be indicated by circles.

Modifications of First Embodiment

Figure 9:
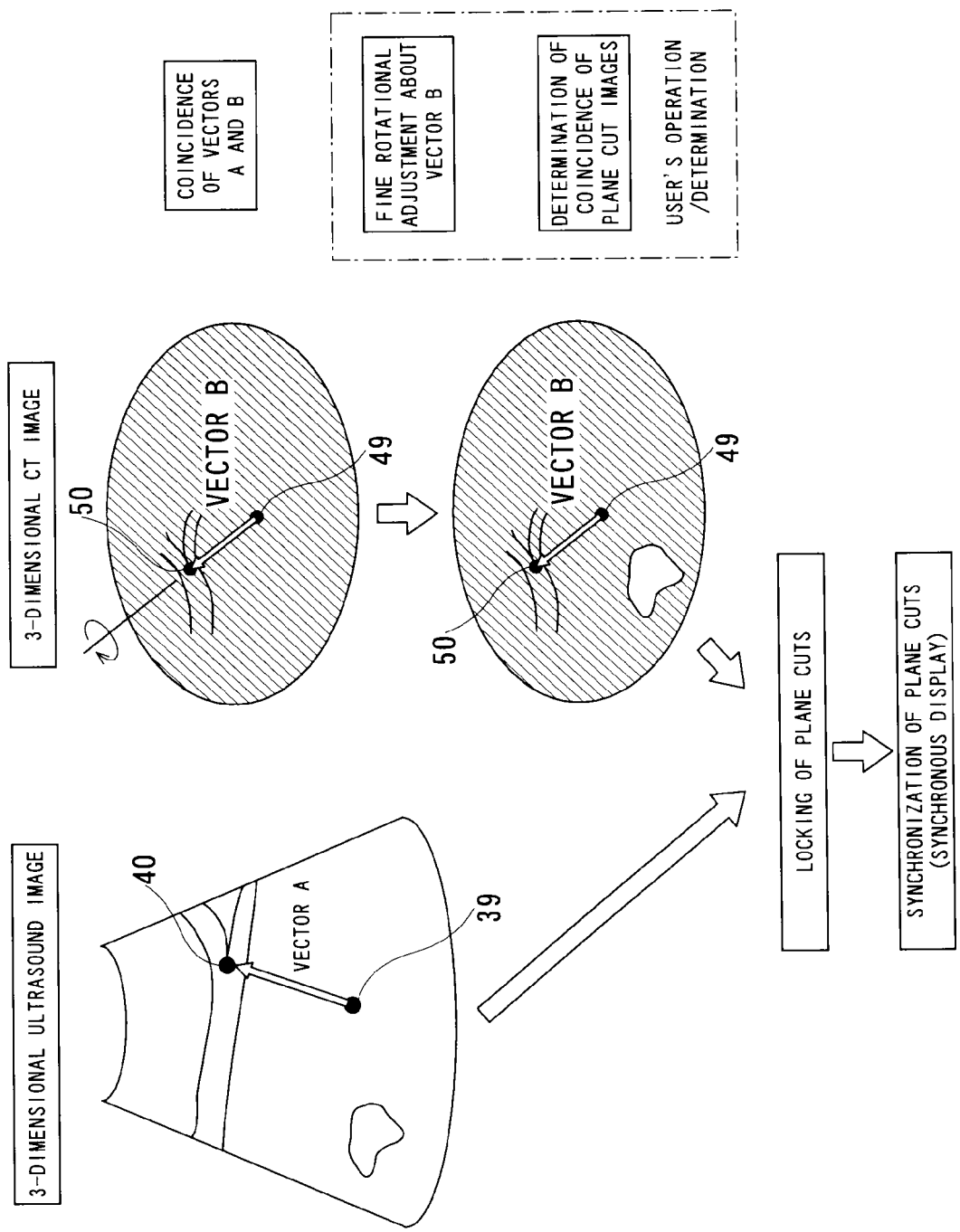
FIG. 9 illustrates an operational concept of the first embodiment.

As illustrated in FIG. 9, in the first embodiment described above, the vector A (connecting the center locking point 39 and the feature point 40) in the 3-dimensional ultrasound image and the vector B (connecting the center locking point 49 and the feature point 50) in the 3-dimensional CT image are made coincident with each other and then, fine adjustment (by means of rotation) of a plane cut of the 3-dimensional CT image is made about the vector B serving as an axis so that images of the plane cuts of the 3-dimensional CT image and 3-dimensional ultrasound image are made coincident with each other. Since the plane cut of the 3-dimensional CT image is restrained by the vector B, this adjustment (rotation) is less cumbersome for the user and can relatively easily achieve coincidence between these images. Then, the plane cuts are locked upon coincidence therebetween. Since this locking function allows these plane cuts to be synchronously moved, it is made possible to synchronously display the plane cuts of the 3-dimensional CT image and 3-dimensional ultrasound image.

The following modifications further advance the concept of the first embodiment by eliminating the need for fine adjustment of a plane cut of the 3-dimensional CT image.

First Modification of First Embodiment

Figure 10:
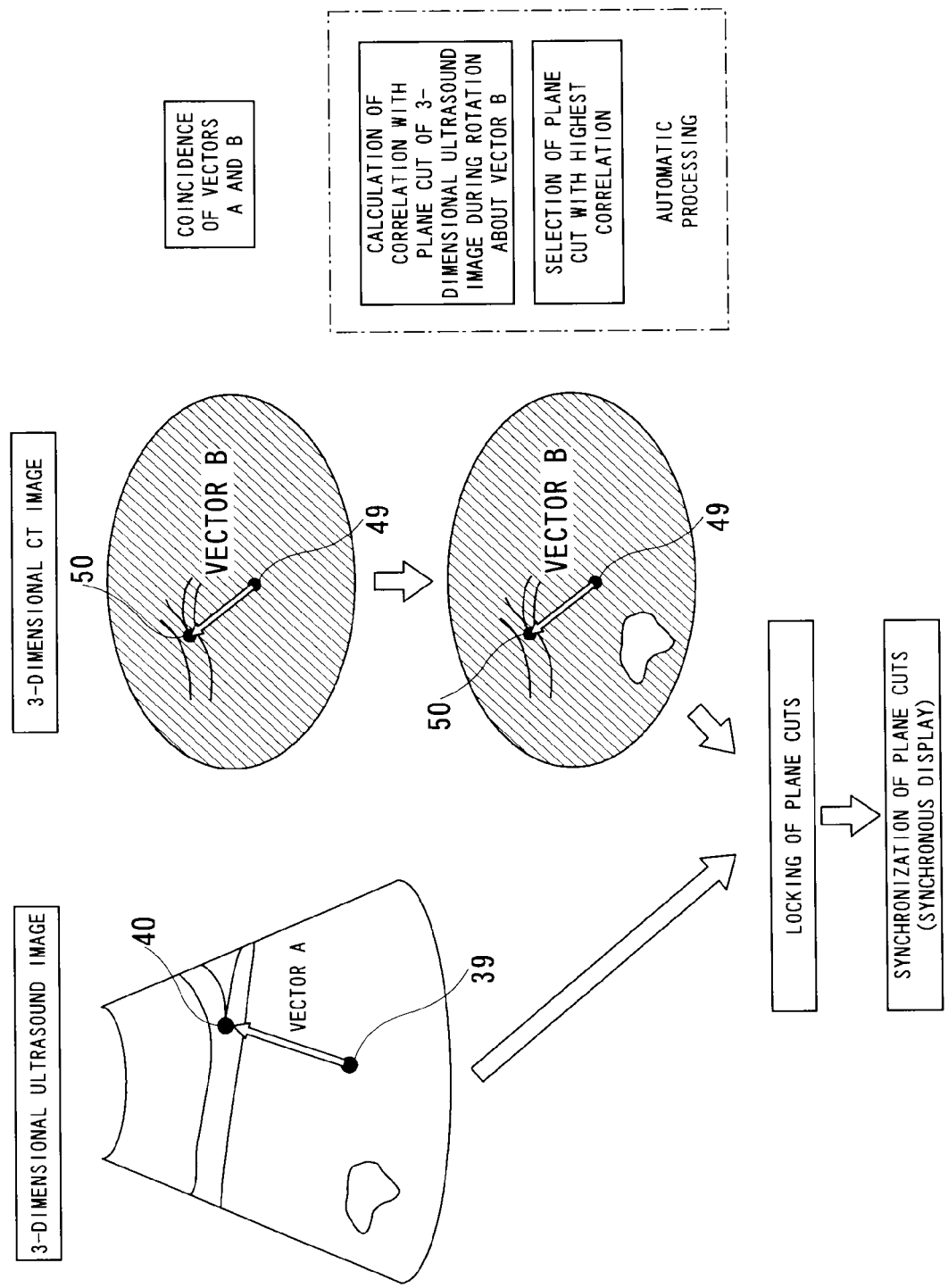
FIG. 10 illustrates an operational concept of a first modification of the first embodiment.

FIG. 10 illustrates an operational concept of a first modification of the first embodiment. In this first modification, after the vector A and the vector B are made coincident with each other, the correlation between the plane cut of the 3-dimensional CT image and that of the 3-dimensional ultrasound image is repeatedly calculated while the plane cut of the 3-dimensional CT image is being rotated about the vector B. Then, in the 3-dimensional CT image, a plane cut located at a position where the highest correlation is found is set as a plane cut that coincides with that of the 3-dimensional ultrasound image. The subsequent processing is the same as that of the first embodiment.

Second Modification of First Embodiment

Figure 11:
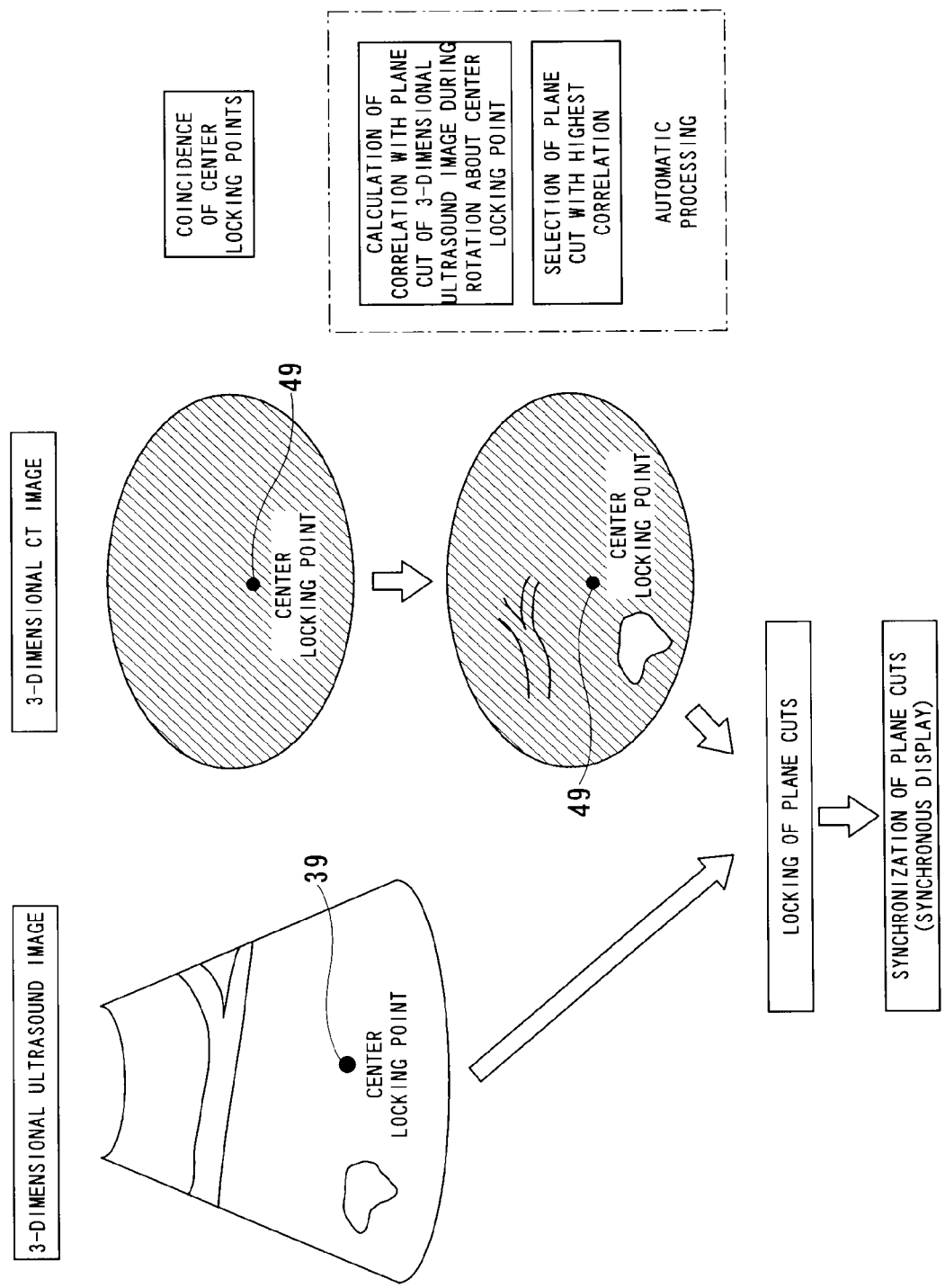
FIG. 11 illustrates an operational concept of a second modification of the first embodiment.

FIG. 11 illustrates an operational concept of a second modification of the first embodiment. The second modification further advances the concept of the first modification in that although the vectors A and B are made coincident with each other in the first modification, only the center locking point 39 and the center locking point 49 are made coincident in the second modification. Next, the correlation between the plane cut of the 3-dimensional CT image and that of the 3-dimensional ultrasound image is repeatedly calculated while the plane cut of the 3-dimensional CT image is being rotated about the center locking point 49 (i.e., rotated about two independent axes). Then, in the 3-dimensional CT image, a plane cut located at a position where the highest correlation is found is set as a plane cut that coincides with that of the 3-dimensional ultrasound image. The subsequent processing is the same as that of the first embodiment. Although the calculation load in the second modification may be higher than that in the first modification, the operational burden on the user can be reduced, as coincidence between two points can be achieved relatively easily.

Third Modification of First Embodiment

Figure 12:
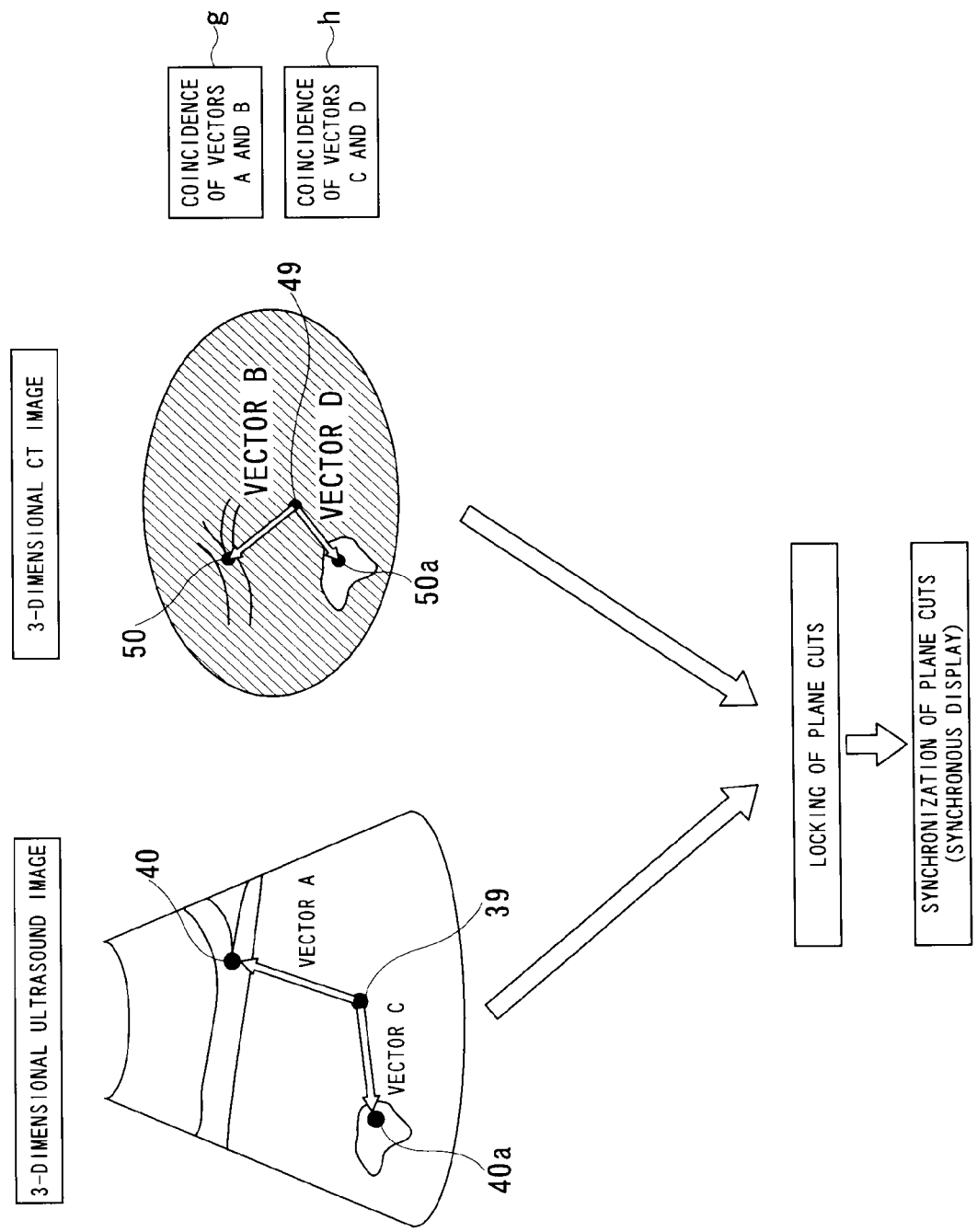
FIG. 12 illustrates an operational concept of a third modification of the first embodiment.

FIG. 12 illustrates an operational concept of a third modification of the first embodiment. In the third modification, first, a vector C and a vector D as well as the vectors A and B are made coincident with each other. The vector C is a vector directed from the center locking point 39 to a second feature point 40$a$, while the vector D is a vector directed from the center locking point 49 to a second feature point 50$a$. By making two vectors in the same plane coincident with each other, an exact coincidence between the plane cuts of the 3-dimensional ultrasound image and 3-dimensional CT image can be achieved.

Although an operational burden on the user may be slightly increased as a coincidence between two vectors needs to be made, the third modification can eliminate the need for correlation processing.

Second Embodiment

Figure 13:
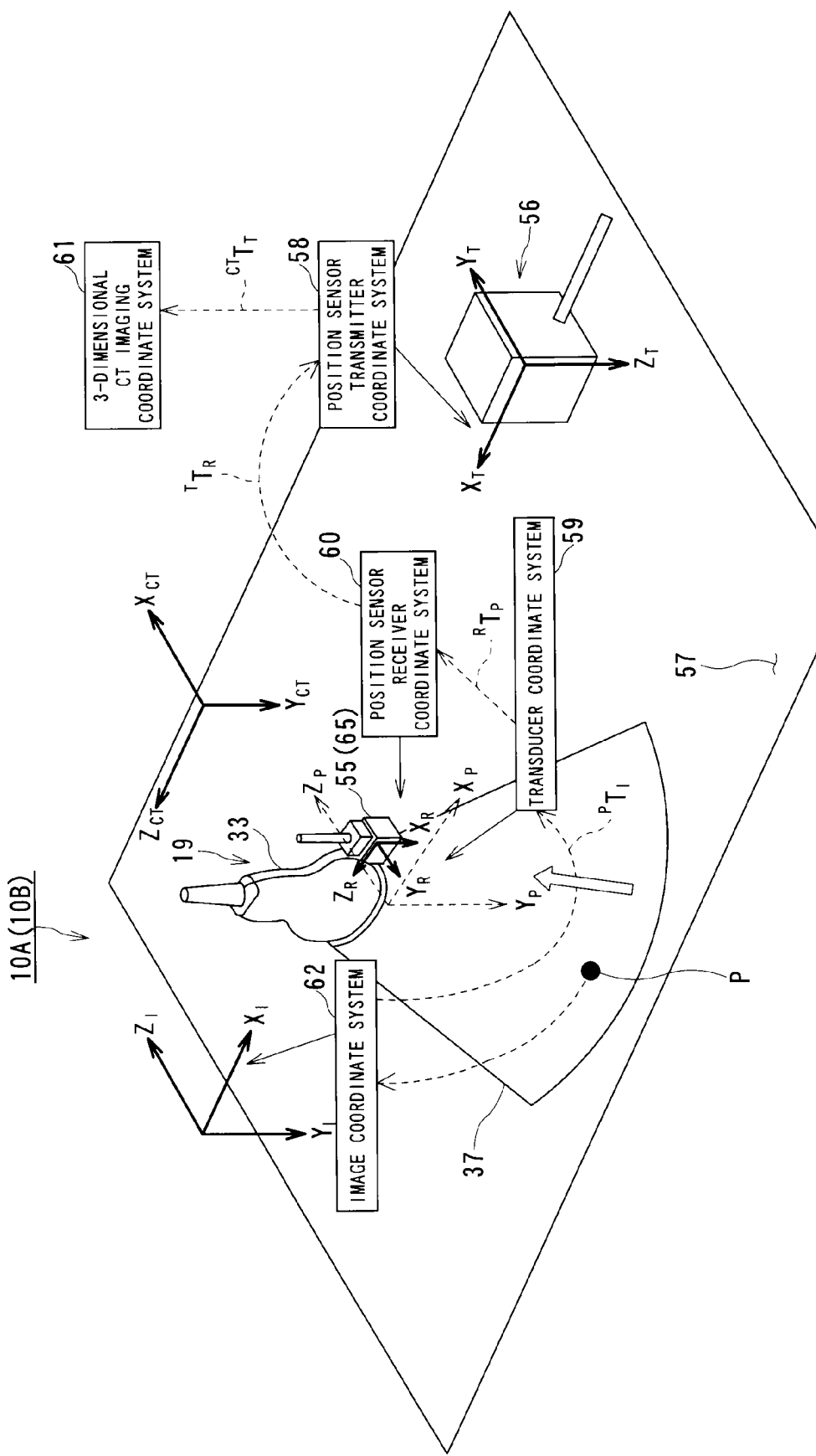
FIG. 13 illustrates a 3-dimensional diagnostic imaging system according to a second embodiment of the present invention and shows a relationship of an ultrasound cross section and a 3-dimensional CT imaging space coordinates obtained from a 3-dimensional position sensor.

FIG. 13 illustrates a 3-dimensional diagnostic imaging system according to a second embodiment of the present invention.

Since an overall structure and functions of a 3-dimensional diagnostic imaging system 10A are similar to those of the 3-dimensional diagnostic imaging system 10 illustrated in FIG. 1 to FIG. 3, like components are given the same reference numerals and their description will be simplified or omitted.

In the 3-dimensional diagnostic imaging system 10A of the second embodiment, the ultrasound transducer 33 (such as a 1-dimensional array transducer, a 4-dimensional mechanical transducer, or a real-time 3-dimensional transducer with 2-dimensional array ultrasound transducer) of the ultrasound diagnostic imaging apparatus 19 is provided with a position sensor receiver 55 serving as a 3-dimensional position sensor, through which the 3-dimensional position of the ultrasound transducer 33 can be automatically detected by a position sensor transmitter 56 on a reference bed 57 serving as a reference.

The position sensor transmitter 56 of the ultrasound diagnostic imaging apparatus 19 forms a 3-dimensional $X_T$-$Y_T$-$Z_T$ position sensor transmitter coordinate system 58 on the reference bed 57. The 3-dimensional position of the ultrasound transducer 33 is defined in an $X_P$-$Y_P$-$Z_P$ transducer coordinate system 59. The 3-dimensional position of the position sensor receiver 55 attached to the ultrasound transducer 33 is defined in an $X_R$-$Y_R$-$Z_R$ position sensor receiver coordinate system 60. A transducer image obtained by the ultrasound transducer 33 is transformed into coordinates in an $X_I$-$Y_I$-$Z_I$ image coordinate system 62. A 3-dimensional CT image obtained by the shifting and rotating operation of the ultrasound transducer 33 is defined, through the transducer coordinate system 59, position sensor receiver coordinate system 60, and position sensor transmitter coordinate system 58, in a 3-dimensional CT imaging coordinate system 61.

A feature point P on the 3-dimensional CT image is defined, through an image coordinate system 62, transducer coordinate system 59, position sensor receiver coordinate system 60, and position sensor transmitter coordinate system 58, in the 3-dimensional CT imaging coordinate system 61. Transformation between the image coordinate system 62, transducer coordinate system 59, position sensor receiver coordinate system 60, position sensor transmitter coordinate system 58, and 3-dimensional CT imaging coordinate system 61 is performed in the main body 30 of the ultrasound diagnostic imaging apparatus 19.

A typical workflow of the 3-dimensional diagnostic imaging system 10A having the position sensor receiver 55 differs from that of the 3-dimensional diagnostic imaging system 10 in processing relating to steps S3 to S10. Except for this, the workflows of the 3-dimensional diagnostic imaging systems 10A and 10 are substantially the same.

In the 3-dimensional diagnostic imaging system 10A, immediately before or after the 3-dimensional ultrasound image 36 (see FIG. 4A) is acquired and displayed e.g., on the left side of the monitor 32, an image of an ultrasound cross section appropriate for being a reference cross section is formed by a real-time 2-dimensional imaging technique, which is a typical ultrasound imaging technique, and displayed. The position and rotational direction of this ultrasound cross section in the imaging space of a 3-dimensional CT image are automatically calculated by a calculation control unit of the main body 30 of the ultrasound diagnostic imaging apparatus 19 on the basis of 3-dimensional position sensor information from the position sensor receiver (receiver coil) 55 (see FIG. 13) attached to the ultrasound transducer 33.

The position and rotational direction of the positioning cross section of the ultrasound image are calculated on the premise, as illustrated in FIG. 13, that the relationship between the 3-dimensional position sensor measurement coordinate space and the 3-dimensional CT imaging coordinate space (i.e., transformation matrix $^{CT}T_T$ for transformation between these 3-dimensional coordinate spaces) is already known.

For example, if the positional relationship between the reference bed 57 and a transmission system for defining the space (3-dimensional) coordinates of the position sensor receiver 55 is determined in advance, the transformation matrix $^{CT}T_T$ described above can be used as a fixed value.

Then, on the basis of the position and rotational direction of the positioning cross section of the ultrasound image, a directional vector in the ultrasound cross section with respect to a CT cross section is calculated. From the direction and position of the directional vector relative to the CT cross section, a CT cross section with an image substantially identical to that of the ultrasound cross section can be obtained and automatically displayed.

After the ultrasound cross section image and the CT cross section image are displayed on the left and right sides of the monitor 32 of the ultrasound diagnostic imaging apparatus 19, a line connecting a rotation center (i.e., diagnosis point) and a feature point is graphically displayed as a directional vector line. In the subsequent steps, image processing is performed in the same manner as that in step S11 and the following steps of the first embodiment. By comparing the cross sections of the 3-dimensional ultrasound image and 3-dimensional CT image (or 3-dimensional MRI image) displayed as described above, the user can efficiently and effectively identify an affected part and make a differential diagnosis of a disease, such as cancer.

Modifications of Second Embodiment

A 3-dimensional diagnostic imaging system according to a modification the second embodiment of the present invention will now be described.

A 3-dimensional diagnostic imaging system 10B according to this modification is realized by adding a 3-dimensional direction sensor 65 to the ultrasound transducer 33 of the ultrasound diagnostic imaging apparatus 19 in the 3-dimensional diagnostic imaging system 10A of the second embodiment. Other components and functions of the 3-dimensional diagnostic imaging system 10B are similar to those of the 3-dimensional diagnostic imaging system 10A. Like components are given the same reference numerals and their description will be simplified or omitted.

In the 3-dimensional diagnostic imaging system 10B, the ultrasound transducer 33 may be a 1-dimensional array transducer, a 4-dimensional mechanical transducer, or a real-time 3-dimensional transducer. This ultrasound transducer 33 is provided with the 3-dimensional direction sensor 65, instead of the position sensor receiver 55 in the 3-dimensional diagnostic imaging system 10A.

A typical workflow of the 3-dimensional diagnostic imaging system 10B having the 3-dimensional direction sensor 65 differs from that of the 3-dimensional diagnostic imaging system 10 in processing relating to steps S3 to S10. Except for this, the workflows of the 3-dimensional diagnostic imaging systems 10B and 10 are substantially the same.

In the 3-dimensional diagnostic imaging system 10B, immediately before or after the 3-dimensional ultrasound image 36 is acquired and displayed (see step S3 of the first embodiment) on the monitor 32 of the ultrasound diagnostic imaging apparatus 19, an ultrasound image formed by a real-time 2-dimensional imaging technique, which is a typical ultrasound imaging technique, is displayed. Then, in the ultrasound image, an image of a cross section appropriate for being a reference cross section is taken and displayed.

The rotational direction of this cross section of the ultrasound image in the corresponding 3-dimensional CT imaging space is automatically calculated on the basis of 3-dimensional direction sensor information from the 3-dimensional direction sensor 65 attached to the ultrasound transducer 33.

The rotational direction of the positioning cross section of the ultrasound image is calculated on the premise that the relationship between the 3-dimensional direction sensor measurement coordinate space and the 3-dimensional CT imaging coordinate space (i.e., rotation matrix between these 3-dimensional coordinate spaces) is already known. Under this premise, if the relationship between the reference bed 57 and a transmission system for defining the space (3-dimensional) coordinates of the 3-dimensional direction sensor 65 is determined in advance, the rotation matrix described above can be used as a fixed value.

Then, on the basis of the rotational direction of the positioning cross section of the ultrasound image, a directional vector in the ultrasound cross section with respect to a 3-dimensional CT cross section is calculated. From the direction of the directional vector, an image of the 3-dimensional CT cross section oriented in substantially the same direction as that of the ultrasound cross section can be automatically displayed.

Additionally, by performing shifting operation on the 3-dimensional CT image, it is possible to locate a 3-dimensional CT cross section with an image substantially identical to that of the ultrasound cross section.

After the ultrasound cross section image and the 3-dimensional CT cross section image are displayed on the left and right sides of the monitor 32 of the ultrasound diagnostic imaging apparatus 19, a line connecting a rotation center (i.e., diagnosis point) and a feature point is graphically displayed as a directional vector line. In the subsequent steps, image processing is performed in the same manner as that in step S11 and the following steps of the first embodiment.

By comparing the displayed cross sections of the 3-dimensional ultrasound image and 3-dimensional CT image (or 3-dimensional MRI image) that are complementary to each other, the user can efficiently and effectively identify an affected part and make a differential diagnosis of a disease, such as cancer.

In the second embodiment and modifications of the present invention described above, one of two 3-dimensional images to be compared is a 3-dimensional ultrasound image acquired by an ultrasound imaging modality and the other is a 3-dimensional image acquired by another type of diagnostic imaging modality, such as a 3-dimensional CT image or a 3-dimensional MRI image. Alternatively, 3-dimensional images to be compared may be those acquired by the same diagnostic imaging modality, such as an ultrasound diagnostic imaging apparatus, but at different time points.

For example, when contrast-enhanced ultrasound 3-dimensional images are sequentially taken during a single medical diagnostic test, images taken before and after a treatment may be compared for evaluation of effects of the treatment, such as RFA. Thus, the user can effectively and efficiently identify an affected part and make a differential diagnosis of a disease, such as cancer.

In the 3-dimensional diagnostic imaging system of the present invention, the following steps may be performed:

1. Contrast-enhanced ultrasound 3-dimensional images are sequentially taken and temporarily stored in the storage medium 20, and volumes of two different time phases are extracted from the storage medium 20 and simultaneously displayed;

2. A single point in an affected part is specified in a plane cut of one of two VR images (3-dimensional CT images or 3-dimensional MRI images), the plane cut is rotated about the specified point, and a cross section image appropriate for use as a diagnostic image is displayed; and 3. Then, a synchronization display/control function is activated so that contrast-enhanced ultrasound 3-dimensional images of two different time phases are displayed and manipulated synchronously, and so that an affected part can be located and a differential diagnosis of a disease can be made effectively and efficiently.

JP-A 2005-169070 or US 2005/0033160 A1 discloses a technique in which a 2-dimensional ultrasound image and a 3-dimensional image (e.g., 3-dimensional CT image) are associated with each other and displayed. For associating the 2-dimensional ultrasound image and 3-dimensional image with each other, this technique involves not only making these images coincident with each other, but also using a position sensor for detecting the location and position of an ultrasound transducer. On the other hand, the 3-dimensional diagnostic imaging system according to the first embodiment of the present invention eliminates the need for such a position sensor while it still needs to perform operations to achieve coincidence between vectors A and B and make a fine adjustment of images. Although the 3-dimensional diagnostic imaging system according to the second embodiment of the present invention has a position sensor and uses vectors A and B, there is no need to perform any operation to achieve coincidence between vectors A and B.

As described above, the 3-dimensional diagnostic imaging system according to the embodiments of the present invention allows for an easy comparison between any corresponding cross sections of complementary 3-dimensional images, that is, a 3-dimensional ultrasound image showing a specific local area and a 3-dimensional diagnostic modality image showing an overall view.

The present invention is not limited only to the embodiments described above but may be embodied, in the practical phase, by modifying constituent elements without departing from the scope of the present invention. A variety of other embodiments can be realized by combining a plurality of constituent elements disclosed in the embodiments described above. For example, some of the constituent elements disclosed in the embodiments may be omitted, or constituent elements disclosed in different embodiments may be combined.

What is claimed is:

1. A 3-dimensional diagnostic imaging system for acquiring and displaying 3-dimensional images, the system comprising:

an ultrasound diagnostic imaging apparatus configured to display a first cross section of a first 3-dimensional image extracted from a first volume data including an affected part of a subject;

a 3-dimensional medical diagnostic imaging apparatus configured to display a second cross section of a second 3-dimensional image extracted from a second volume data obtained by medical diagnostic imaging modalities other than the ultrasound diagnostic imaging apparatus, the second cross section being substantially identical to the first cross section displayed by the ultrasound diagnostic imaging apparatus; and an image processing/display unit configured to specify a first center locking point and a first feature point in the first 3-dimensional image and to further specify a second center locking point and a second feature point in the second 3-dimensional image, the first center locking point and the first feature point respectively corresponding to the second center locking point and the second feature point, to adjust the first cross section which includes the first center locking point and the first feature point and the second cross section which includes the second center locking point and the second feature point so that the first and second cross sections are made coincident with each other, and to synchronously move, after adjustment of the first and second cross sections, the first 3-dimensional image and the second 3-dimensional image which are simultaneously displayed on a monitor of the image processing/display unit, wherein the image processing/display unit includes a vector specifying unit configured to specify a first directional vector which connects the first center locking point and the first feature point in the first volume data and a second directional vector which connects the second center locking point and the second feature point in the first volume data, and the image processing/display unit adjusts the first and second cross sections by making the first and second directional vectors coincident with each other, and wherein the image processing/display unit calculates correlation between a first plane cut in the first 3-dimensional image and a second plane cut in the second 3-dimensional image while rotating the second plane cut about the second directional vector, and determines the first plane cut and the second plane cut which are obtained with the highest correlation as the first and second cross sections which are coincident with each other.

2. The 3-dimensional diagnostic imaging system according to claim 1, further comprising a locking unit,
wherein the locking unit relates the first and second 3-dimensional images displayed on the monitor so that the first and second 3-dimensional images mutually track each other's movements.

3. The 3-dimensional diagnostic imaging system according to claim 2, wherein the image processing/display unit includes an unlocking unit configured to cancel a locked state or a tracking controlled state of the first and second 3-dimensional images.

4. The 3-dimensional diagnostic imaging system according to claim 1, wherein the image processing/display unit includes a spherical region display unit configured to display spherical regions in the respective first and second 3-dimensional images that can be displayed synchronously, the spherical regions each having a center about which the corresponding cross section is rotated.

5. The 3-dimensional diagnostic imaging system according to claim 1, wherein the image processing/display unit includes an intersection line display unit configured to display, in the respective cross sections of the first and second 3-dimensional images that can be displayed synchronously, lines of intersection of the cross sections and respective spherical regions displayed therein, the spherical regions each having a center about which the corresponding cross section is rotated.

6. The 3-dimensional diagnostic imaging system according to claim 1, wherein the ultrasound diagnostic imaging apparatus includes:
a main body;
an ultrasound transducer connected to the main body; and
a 3-dimensional position sensor attached to the ultrasound transducer.

* * * * *